United States Patent [19]
Field

[11] Patent Number: 5,750,884
[45] Date of Patent: May 12, 1998

[54] COMPLEX VISCOSITY AND COMPLEX MODULUS MEASUREMENT DEVICE AND METHOD

[75] Inventor: John S. Field, Berowra Heights, Australia

[73] Assignee: Commonwealth Scientific and Industrial Research Organisation, Campbell, Australia

[21] Appl. No.: 727,539

[22] PCT Filed: Apr. 19, 1995

[86] PCT No.: PCT/AU95/00232

§ 371 Date: Nov. 25, 1996

§ 102(e) Date: Nov. 25, 1996

[87] PCT Pub. No.: WO95/28629

PCT Pub. Date: Oct. 26, 1995

[30] Foreign Application Priority Data

Apr. 19, 1994 [AU] Australia ................ PM 5178

[51] Int. Cl.⁶ ...................... G01N 11/00; G01N 9/24
[52] U.S. Cl. .................. 73/54.24; 73/54.14; 73/54.34
[58] Field of Search .................. 73/54.24, 54.14, 73/54.25, 54.27, 54.34

[56] References Cited

U.S. PATENT DOCUMENTS

| | | | |
|---|---|---|---|
| 3,107,520 | 10/1963 | Mouly et al. | 73/60 |
| 3,194,064 | 7/1965 | Miles | 73/101 |
| 3,479,858 | 11/1969 | Masashiumeno et al. | 73/15.6 |
| 3,699,808 | 10/1972 | Ford et al. | 73/91 |
| 3,903,731 | 9/1975 | Sieben | 73/54 |
| 4,601,195 | 7/1986 | Garritano | 73/60 |
| 4,602,501 | 7/1986 | Hirata | 73/54 |
| 4,637,250 | 1/1987 | Irving, Jr. et al. | 73/57 |
| 4,754,640 | 7/1988 | Fitzgerald et al. | 73/54 |
| 4,794,788 | 1/1989 | Masters et al. | 73/59 |
| 4,862,735 | 9/1989 | Williams et al. | 73/54 |
| 4,905,499 | 3/1990 | Miura et al. | 73/32 A |
| 5,038,295 | 8/1991 | Husband et al. | 364/508 |
| 5,067,344 | 11/1991 | Fitzgerald et al. | 73/54 |
| 5,177,997 | 1/1993 | Maciejewski | 73/54.24 |
| 5,287,749 | 2/1994 | Nakamura | 73/808 |

FOREIGN PATENT DOCUMENTS

| | | |
|---|---|---|
| 43319/89 | 4/1991 | Australia . |
| 58-10630 | 1/1983 | Japan . |
| 589-568 | 1/1978 | U.S.S.R. . |
| 1226901 | 3/1971 | United Kingdom . |
| WO94/14047 | 6/1994 | WIPO . |

*Primary Examiner*—Hezron E. Williams
*Assistant Examiner*—J. David Wiggins
*Attorney, Agent, or Firm*—Dressler, Rockey, Milnamow & Katz, Ltd.

[57] ABSTRACT

The viscometer (100) includes a difference amplifier (110) driven by a signal generator (111) which supplies a control signal to shaker (120), which is sufficiently powerful to impose such strains as may be demanded by a controlling reference voltage with a desired form. The shaker (120) drives a shaft (125), and an upper plate (130) is attached to a distal end of the shaft (125). A lower plate (140) is positioned adjacent, and substantially parallel to, upper plate (130), thereby creating a space that may be filled by fluid sample (150). The motion of the upper plate h(t) is measured by a sensor (180). Plate (140) is mounted on force measuring means (160) which keeps lower plate (140) substantially motionless relative to frame (165). Force measuring means (160) provides an output, or force, signal f(t) that is indicative of the force which fluid sample (150) exerts on plate (130 and 140) in response to the movement of upper plate (130). This force is related to the viscosity of fluid sample (150) by the equation $G^*(\omega)=h^3/3\pi a^4 \ F(\omega)/H(\omega)$, where $G^*(\omega)$ is the complex modulus, $F(\omega)$ is the Fourier transform of f(t), $H(\omega)$ is the Fourier transform of h(t), a is the radius of the plate (130), and h is the mean distance between the plates (130 and 140).

23 Claims, 6 Drawing Sheets

FLUID 1.
MINERAL OIL

FLUID 2
BOGER FLUID

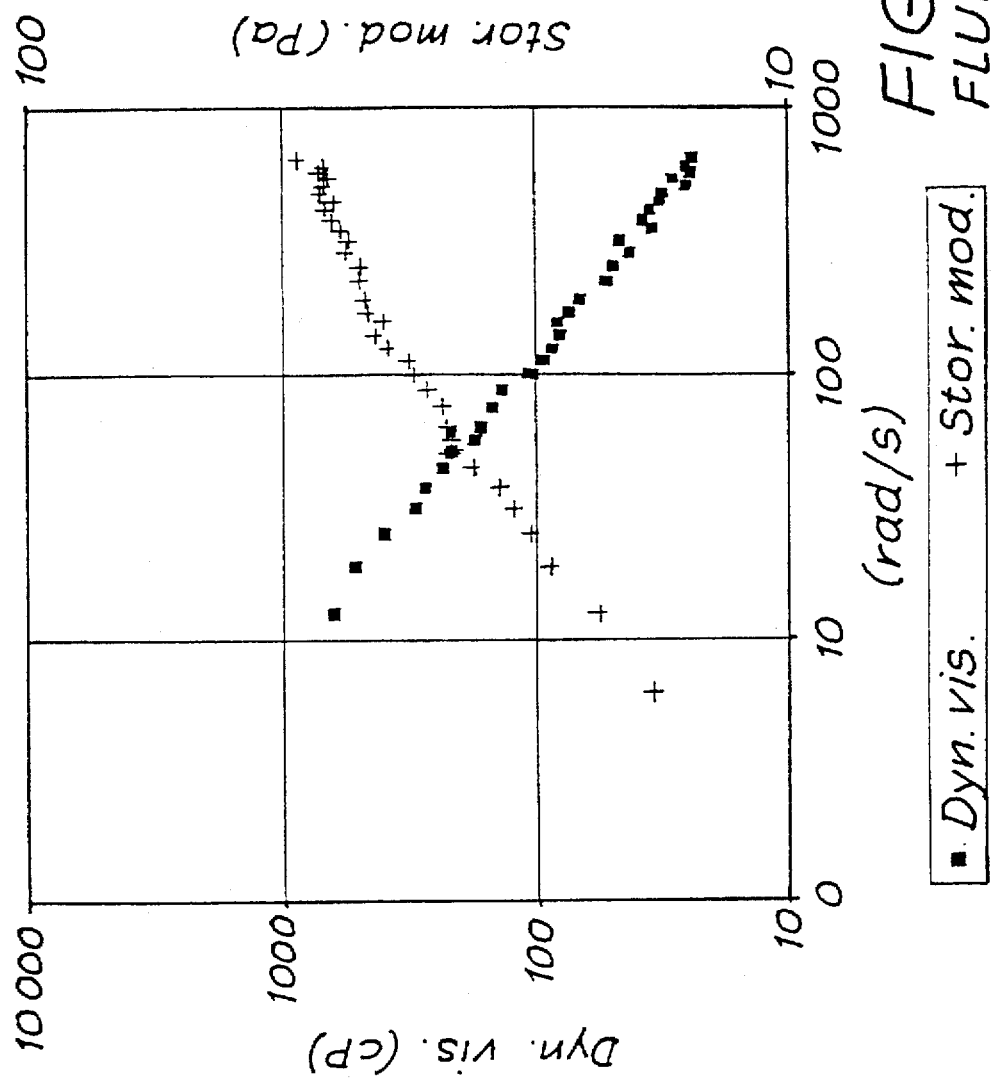

COMPLEX VISCOSITY AND COMPLEX MODULUS MEASUREMENT DEVICE AND METHOD

FIELD OF THE INVENTION

The present invention relates to the measurement of viscosity and, in particular, to a method and apparatus for measuring the complex viscosity and complex modulus of small volumes of fluids.

BACKGROUND OF THE INVENTION

The viscosity of a fluid is the resistance that it offers to flow when the fluid is subjected to a shear stress. For a fluid occupying an incremental volume between two plates of area A separated by distance dx, where the plates are moving in planes parallel to their respective surfaces with velocity difference dv, the force $f$ exerted by the fluid on the plates is $$f = \eta A \frac{dv}{dx}$$

where $\eta$, the fluid's viscosity is substantially constant at a given temperature and is independent of shear rate. Fluids which satisfy this relationship are termed Newtonian but these only include a fraction of all possible fluids. In particular many fluids exhibit elasticity in addition to a viscosity which may not be independent of shear rate. It is then conventional to measure complex viscosity in an apparatus in which the plates move parallel to the plane of their surface with a relative oscillatory velocity difference. A complex viscosity is defined which includes both a magnitude and a phase component.

Conventional apparatus for measuring fluid viscosity (i.e., viscometers) include Ostwald's viscometer which uses Poiseuille's formula relating flow rate through a pipe to the fluid's viscosity, and the falling-sphere viscometer which uses Stokes' law relating the terminal velocity of a sphere falling though a fluid to the fluid's viscosity.

Both of the these conventional types of viscometers work on the assumption that the fluid's viscosity is substantially constant at a given temperature. They cannot be used for measuring viscosities of non-Newtonian fluids. In addition, these viscometers require a large sample of fluid in order to provide accurate viscosity measurements. Determinations of complex viscosity can be time-consuming and often only small quantities of the fluid are available for measurement.

Thus, there is a need for a viscometer that can provide rapid measurements of complex viscosity for a non-Newtonian fluid, and for a viscometer that utilises only a small amount of fluid.

SUMMARY OF THE INVENTION

The present invention consists in a viscometer for determining a complex viscosity of a fluid, the viscometer comprising: vibrating means for imparting an alternating movement to a surface of the fluid to cause a corresponding alternating flow of the fluid, the flow leading the fluid to exert on the vibrating means an alternating reaction force related to the viscosity of the fluid; force measuring means for providing a force signal related to the alternating reaction force; displacement measuring means for providing a movement signal related to the alternating movement of the surface; and processing means for using the force signal and the movement signal to compute the complex viscosity of the fluid.

Preferably, the alternating movement of the surface of the fluid is in a direction substantially perpendicular to the surface.

Preferably, the vibrating means comprises an electromechanical shakers which is further preferably responsive to a control signal. The control signal is preferably a random or pseudo-random signal.

Preferably, the displacement measuring means comprises an arrangement that exhibits an electrical capacitance that varies in response to the movement of the surface of the fluid.

Preferably, the force measuring means comprises a load cell.

Preferably, the processor computes the Fourier transform $F(\omega)$ of the force signal, the Fourier transform $H(\omega)$ of the movement signal, and the ratio $F(\omega)/H(\omega)$ of the Fourier transform of the force signal to the Fourier transform of the movement signal.

Preferably, the vibrating means comprises two substantially parallel plates one of which has a radius $\alpha$, the plates being separated by a mean distance h, the fluid being maintained between the two plates, and wherein the processor computes a complex modulus $G^*(\omega)$ of the fluid, where $G^*=G$ (real)+i G (imaginary), according to the formula $$G^*(\omega) = \frac{h^3}{3\pi a^4} \frac{F(\omega)}{H(\omega)}.$$

Alternatively, the vibrating means comprises a set of coaxial cylinders.

The present invention further consists in a method for measuring a viscosity of a fluid, the method comprising the steps of: imparting an alternating movement to a surface of the fluid to cause a corresponding alternating flow of the fluid, the flow leading the fluid to produce an alternating reaction force related to the complex viscosity of the fluid; providing a force signal related to the alternating reaction force; providing a movement signal related to the alternating movement of the surface; and processing the force signal and the movement signal to compute the complex viscosity of the fluid.

BRIEF DESCRIPTION OF THE DRAWINGS

The invention will be described with reference to the accompanying drawings in which:

FIGS. 6, 7 and 8 graphically illustrate dynamic viscosity and storage modulus as measured for mineral oil, Boger fluid and Hyaluronic Acid solution respectively.

DETAILED DESCRIPTION OF THE INVENTION

Fluids that exhibit shear strains that are dependent on the rate of change of shear stress are said to have complex viscosity.

Figure 2:
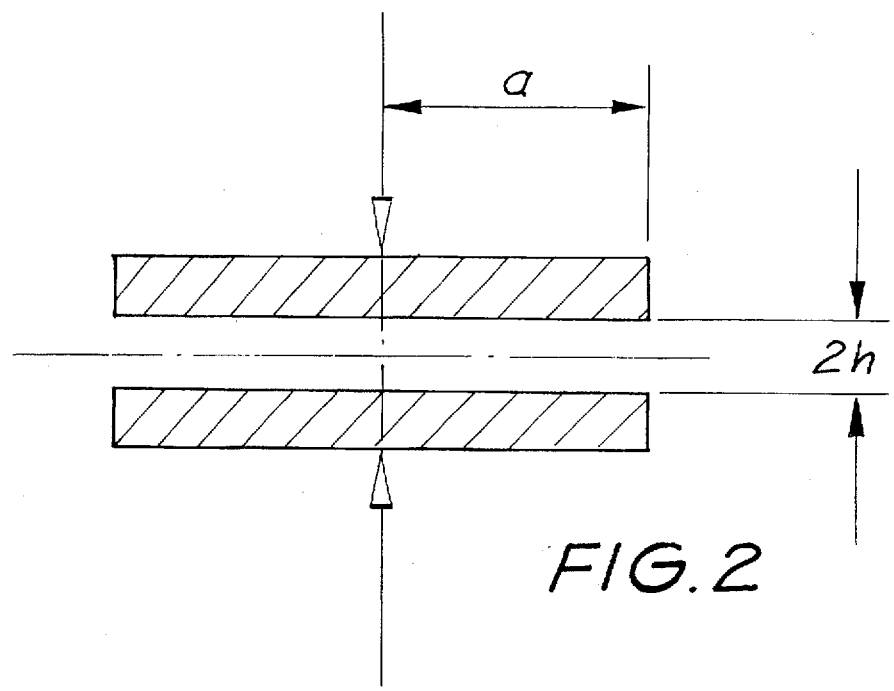
FIG. 2 shows the relationship of plate parameters used in development of the theoretical characteristics of the instrument of FIG. 1.

It is known in the art that for a fluid maintained between two parallel circular plates, a vibratory force applied to the plates in a direction normal to the plane of either of the plates causes the separation between the plates to change at a corresponding rate. The relationship between this applied force $f(t)$ and the corresponding rate $h'(t)=dh(t)/dt$ is given by the expression $$f(t) = \frac{3\pi a^4}{h^3} h'(t)\eta^*$$

where $\alpha$ is the radius of the circular plates, h is the mean separation between the plates (See FIG. 2), and $\eta^*$ is the complex viscosity of the fluid. Taking the Fourier transform of this expression gives $$F(\omega) = \frac{3\pi a^4}{h^3} (i\omega)H(\omega)\eta^*$$

where $F(\omega)$ and $H(\omega)$ are the Fourier transforms of $f(t)$ and $h(t)$ respectively, and $i=\sqrt{-1}$. From this Fourier transform, the complex modulus $G^*(\omega)$ of the fluid, which is defined as the product $$G^*(\omega)=(i\omega)\eta^*,$$

can be written as $$G^*(\omega) = \frac{h^3}{3\pi a^4} \frac{F(\omega)}{H(\omega)}. \tag{1}$$

Thus, the complex modulus can be regarded as the transfer function of a dynamical system that responds to an input signal $H(\omega)$ by producing an output signal proportional to $F(\omega)$. Using this interpretation, the fluid's complex modulus can be determined by applying a vibratory displacement h(t) to the fluid, measuring the resulting force $f(t)$, computing the corresponding Fourier transforms $F(\omega)$ and $H(\omega)$, and computing the complex modulus using equation (1). This is one of the basic principles that are utilised in the present invention.

Figure 1:
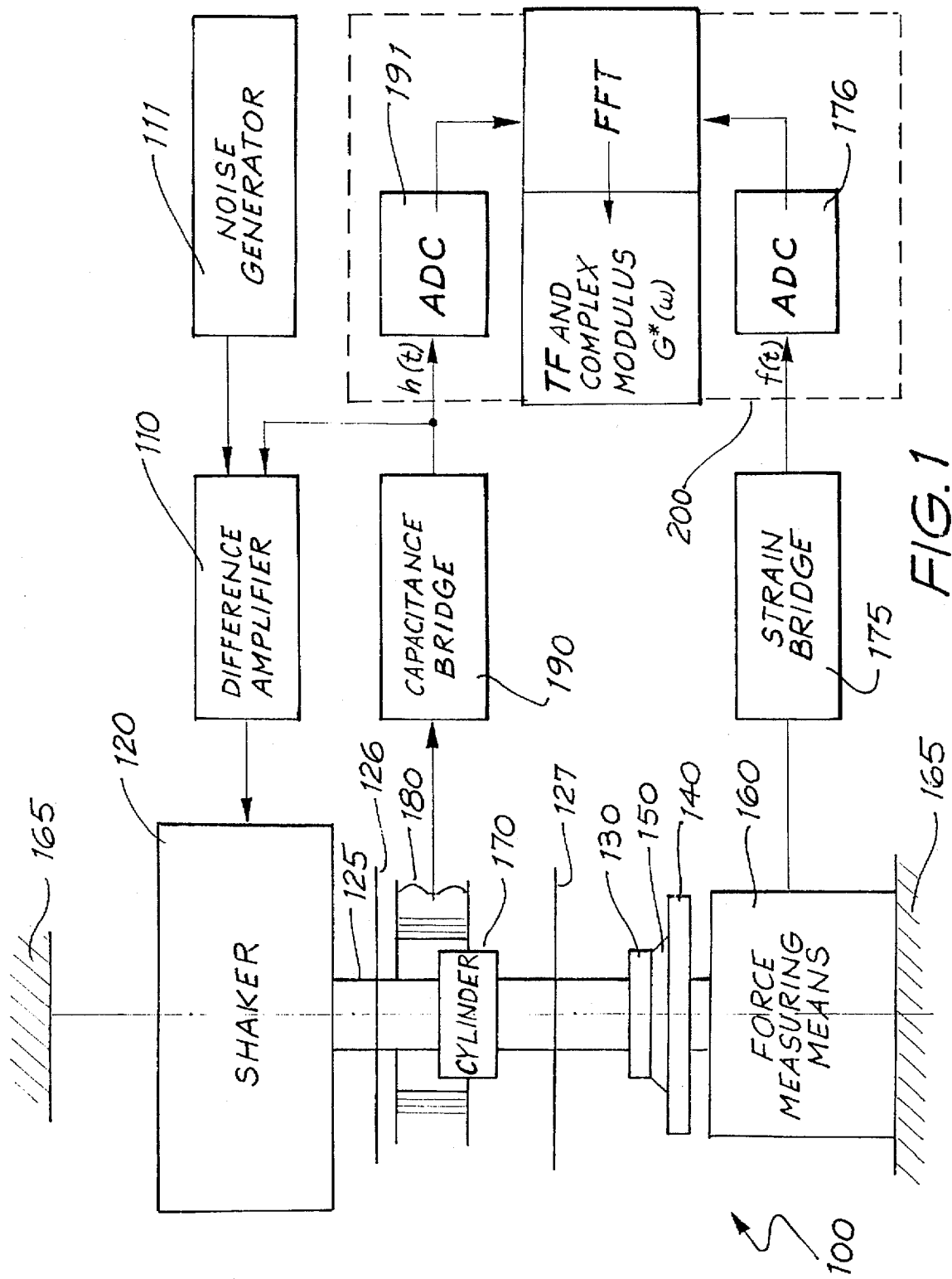
FIG. 1 is a schematic diagram of a viscometer in accordance with the present invention.

FIG. 1 shows a schematic diagram of a preferred embodiment of viscometer 100 in accordance with the present invention. Viscometer 100 includes difference amplifier 110 driven by a signal generator 111 which supplies a control signal to shaker 120. The shaker may be any device that can provide motion. For example, the shaker may be an electromagnetic shaker, or it may be a piezoelectric, magnetostrictive or mechanical shaker. The shaker should be sufficiently powerful to impose such strains as may be demanded by a controlling reference voltage with a desired form.

In the preferred embodiment the shaker has a frequency range of 0.1 to 100 Hz.

Shaker or linear motor 120 drives a shaft 125, which is mounted with a proximal end adjacent shaker 126 and extends through constraints 126 and 127 such that substantially only axial movement of shaft 125 is possible. Shaker 120 causes the shaft 125 to vibrate along its axis in sympathy with the control signal, the vibration being a motion relative to frame 165.

Upper plate 130 is attached toga distal end of the shaft 125. Lower plate 140 is positioned adjacent, and substantially parallel to, upper plate 130, thereby creating a space that may be filled by fluid sample 150. Preferably, plates 130 and 140 are circular and plate 140 may be of larger diameter than plate 130.

Plate 140 is mounted on force measuring means 160 which keeps lower plate 140 substantially motionless relative to frame 165; that is, the force measuring means should have a compliance under the force exerted on plate 140 by fluid sample 150 which is substantially smaller than the motion of plate 130 relative to plate 140. Force measuring means 160 provides an output, or force, signal $f(t)$ that is indicative of the force which fluid sample 150 exerts on plates 130 and 140 in response to the movement of upper plate 130. This force is related to the viscosity of fluid sample 150 by equation (1), where $\alpha$ is the radius of plate 130, and h is the mean distance between plates 130 and 140. Force measuring means 160 should be capable of producing an output signal that is proportional to force from near zero frequency to at least a predetermined upper frequency limit, with minimal phase shift relative to the applied force. Preferably, force measuring means 160 is a piezoelectric load cell, and may be coupled to strain bridge and amplifiers 175 to produce force signal $f(t)$.

The shaft 125 is preferably stepped so as to form cylinder 170 that vibrates axially in sympathy with the control signal. Tube 180 is mounted coaxially with cylinder 170, but remains substantially stationary relative to frame 165 such that a mutual overlap between cylinder 170 and tube 180 varies in sympathy with the movement of upper plate 130. Cylinder 170 and tube 180 are electrically conductive, but are electrically insulated from one another, thereby forming an electrical capacitor whose capacitance is indicative of the mutual overlap, and thus indicative of the movement of upper plate 130. Capacitance determining means 190 is coupled electrically to cylinder 170 and tube 180, and produces an output, or movement, signal h(t) that is indicative of the movement of upper plate 130.

Preferably, capacitance determining means 190 is a capacitance ratio arm transformer bridge. However, any other means may be used fork determining the motion of upper plate 130 and for providing the movement signal. For example, such means may include optical means based on the reflection or transmission of light dependent on the position of upper plate 130. Means for determining the position of upper plate 130 should be capable of producing a signal proportional to the displacement of the upper plate relative to its mean position, from substantially zero frequency to a predetermined upper frequency limit, with minimal phase shift relative to the motion.

Difference amplifier 110 nay incorporate a servo loop which uses negative feedback, compares the movement signal to an input signal and modifies the control signal if necessary to ensure that the movement of upper plate 130 accurately follows the input signal.

The movement and force signals, h(t) and $f(t)$, are fed to processor 200 which calculates the corresponding Fourier transforms, $H(\omega)$ and $F(\omega)$. From these signals, and with knowledge of parameters $\alpha$ and h, the processor can compute the complex modulus $G^*(\omega)$ in accordance with equation (1) for each value of frequency $\omega$. Preferably, processor 200 is a digital processor that includes analog to digital converters 176,191 for converting the force and movement signals (which are usually analogue signals) to equivalent digital signals.

Once $G^*(\omega)$ is determined, it may be divided by (i$\omega$) to produce the complex viscosity $\eta^*$. Both $G^*(\omega)$ and $\eta^*$ may be represented in real and imaginary form, or in any other form that may be required.

In the one embodiment of the invention, fluid sample 150 is held between two flat circular plates, each with a contact radius of 5 mm, and separated by 0.75 mm. Thus, the volume of fluid required for determining viscosity is approximately 0.059 µL. Smaller or larger volumes may be used as required.

However, control of the shape of the fluid/air boundary is found to be easier when the lower plate is larger than the upper plate as illustrated in FIG. 1. If the volume of fluid is sufficient for it to rise a little way up the cylindrical surface of the upper plate the whole of the lower surface of this plate can be more confidently assumed to be in full and effective contact with the fluid. This is achieved by loading a precise volume of fluid, about 10% larger than the volume of the gap, centrally on to the lower plate. It is also important that the edge of the upper plate is sharp.

Boundary conditions are even more difficult to control with sticky fluids and for these, shallow vessels are found to be convenient. These are made by attaching rings, 1.5 mm deep to the lower plate (Ref FIG. 4—not to scale) so that the wall 220 of the vessel so formed is distant from the perimeter of the upper plate by at least 5 times the gap. Sufficient fluid is loaded to fill the vessel to a depth about 10% greater than the gap.

Both piezo-electric and strain gauge load cells may be used with good results. Piezo-electric types offer robustness, high stiffness and good sensitivity but their output rolls off rather quickly at low frequencies. Strain gauge types have a flat response down to zero frequency but are generally fragile and much more compliant. Load cell compliance is undesirable as it introduces additional dynamic responses into both the motion and force measurements.

The spectrum of the upper plate motion in the prototype instrument is not quite flat due to a mechanical resonance in the drive system at 125 Hz. While this resonance does not affect the calculation of transfer functions it was avoided in the present work by limiting the maximum frequency to 100 Hz. The frequency range of the present apparatus is limited to about two decades by the noise base of the analyser although the uppermost frequency may be varied. At low frequencies the force generated is small and at high frequencies with some fluids it (the force) may be high enough to reduce the excursion by overloading the driver. In either case, the noise content of one of the signals is increased and the correlation between them is weakened. Force may be increased or reduced by varying the diameter of the upper plate, or the gap, or both. For example, increasing the upper plate diameter by 50%, and reducing the gap to one half increases the force 40 fold.

Correlation is usually measured by the correlation coefficient $r^2$ which is unity when the two signals are completely correlated and zero when they are uncorrelated. $r^2$ is a useful measure of the quality of the result and was used in the present work. It was found that in generally the results are reliable if $r^2$ is greater than 0.95. However poor correlation is readily seen as noisy transfer functions if these are displayed on a monitor screen as they develop.

Preferably, the distance between the upper and lower plates is adjustable to allow for variation in the thickness of the fluid film. Preferably, a device is included to indicate the relative position of the plates so that their separation can be set to any desired distance.

Figure 4:
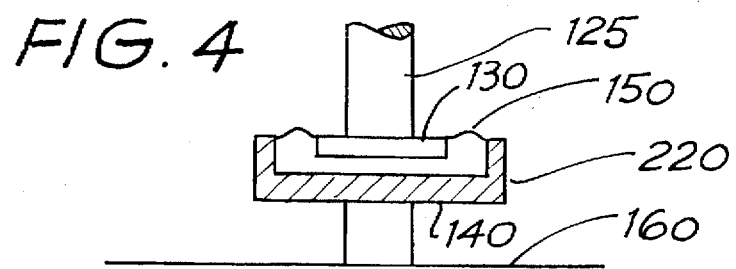
FIG. 4 is an illustration of an alternative embodiment of a fluid sample holder for use in the present invention.
Figure 5:
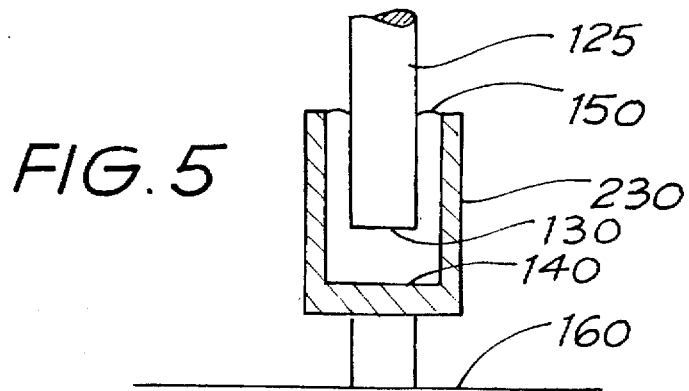
FIG. 5 is an illustration of a second alternative embodiment of a fluid sample holder for use in the present invention.

The vibrating means is not limited to the use of substantially parallel circular plates as illustrated in FIG. 1 or the disk arrangement in FIG. 4. Possible alternative embodiments include vibrating means with a fluid sample holder comprising coaxial cylinders 125 and 230 as shown in FIG. 5. In the embodiment of FIG. 5, outer cylinder 230 is closed at its lower end to form a vessel, but it may be left open.

Preferably, the plates in the vibrating means are removable so as to allow alternative forms of fluid sample holder to be used.

The waveform of the vibration imposed on the fluid by relative motion of the plates may be of any nature providing that it contains sufficient energy at all frequencies in a desired range. Such a waveform may take any of the following forms: a sum of several sinusoids with differing frequencies; a sinusoid with varying frequency; single or reversing ramps; step or impulse functions; or a random function of time. Preferably, a random signal is used to provide perpendicular displacements of opposed parallel plates about a mean displacement such that the strain is continuously changing in a random manner. The random function of time has a predetermined root mean square amplitude, and a power spectrum substantially constant from zero frequency to a predetermined upper frequency limit, and is generated by a digital electronic pseudo-random noise generating circuit that is well known in the art.

Preferably, the mean separation of the plates, the root mean square amplitude of the random function of time, and the upper frequency limit are all variable.

Experimental Results

Although the relationship between $a^4/h^3$ and force implied by equation 1 is well established it has not been previously tested under conditions of small amplitude oscillatory strain. Its applicability in the present case was examined in experiments using light silicone oil. Since plate separation is the easiest parameter to change, the experiments were designed to examine the relationship between the plate separation and the transfer function. Two different upper plates were used, these had diameters, $2a$, of 14.4 and 9.1 mm. With a maximum gap of 1 mm the aspect ratio $2a/h$ had minimum values of 14.4 and 9.1 rising to 28.8 and 18.2 at the smallest gap. The excitation amplitude was constant ranging from 5% to 10% of the gap. The lower plate had a diameter of 23 mm. The validity of the relationship between the radius of the upper plate and the transfer function was inferred by comparing measured and theoretical transfer functions calculated for each combination of gap and upper plate diameter.

The gap was reduced in steps of 0.05 mm from 1 mm to 0.5 mm and equalised transfer functions were obtained at each step. These were developed from 32 excitation sequences at each setting using a maximum frequency of 100 Hz. They were extremely regular and showed typical Newtonian fluid behaviour. Consequently, a single representative value was sufficient to characterise them and the value at a frequency of 90 Hz was taken.

Figure 3:
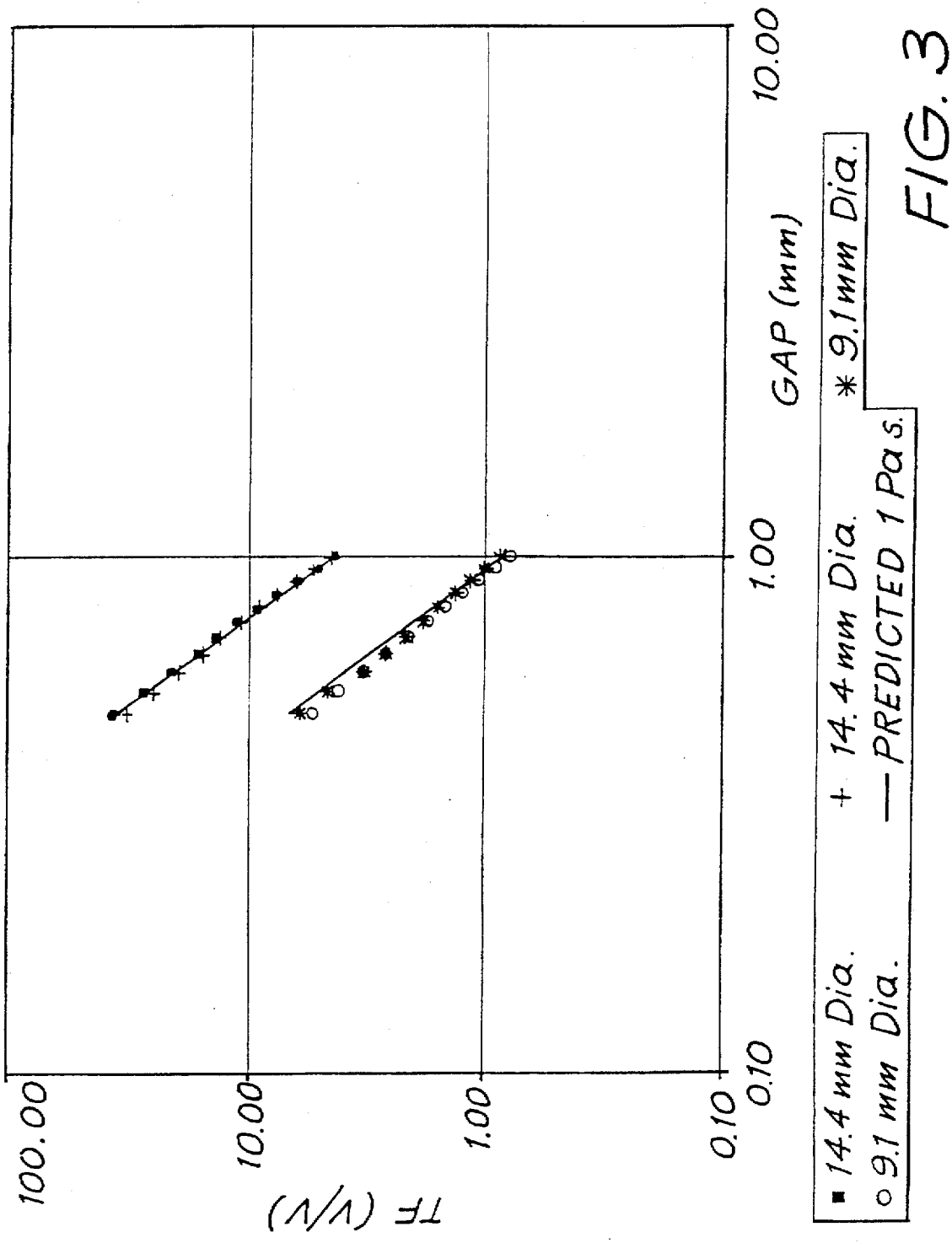
FIG. 3 graphically illustrates the relationship between Log TF and Log gap for two upper plate diameters compared with the theoretically predicted values.

The relationship between Log h and Log TF (magnitude) was found to be linear in all cases with a gradient very close to $-3$, as shown in FIG. 3. The continuous lines superimposed on FIG. 3 were calculated for the two upper plate diameters using the nominal viscosity of 1 Pa as specified for the fluid. The similarity of the data to the calculated values was taken to indicate the suitability of equation 1 for analysing data obtained in tests using the present method and geometries.

Figure 6:
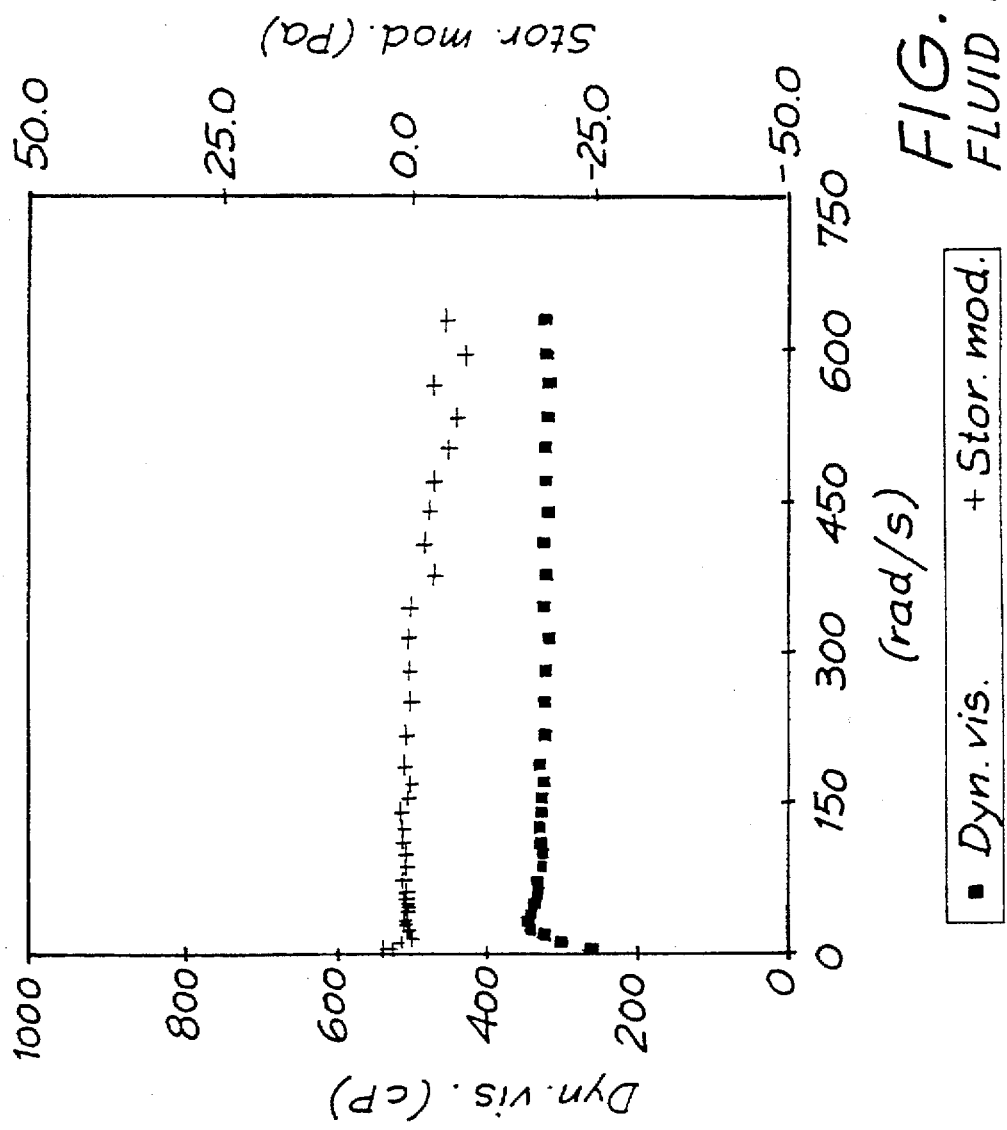

Examples of results obtained with a Fourier Micro-rheometer made in accordance with the present invention will now be described for three fluids of know characteristics a follows:

Fluid 1: A light mineral lubricating oil (Shell Talpa 50). This fluid was measured in the Fourier Micro-rheometer by placing the oil on the lower platen and then using an upper platen of 15 mm diameter and a gap setting of 1 mm. The results for the dynamic viscosity and storage modulus are shown graphically in FIG. 6 over the range from 0 to 750 radians/sec. They show that the oil is substantially a Newtonian fluid with a storage modulus close to zero and a constant dynamic viscosity over the frequency range investigated.

Figure 7:
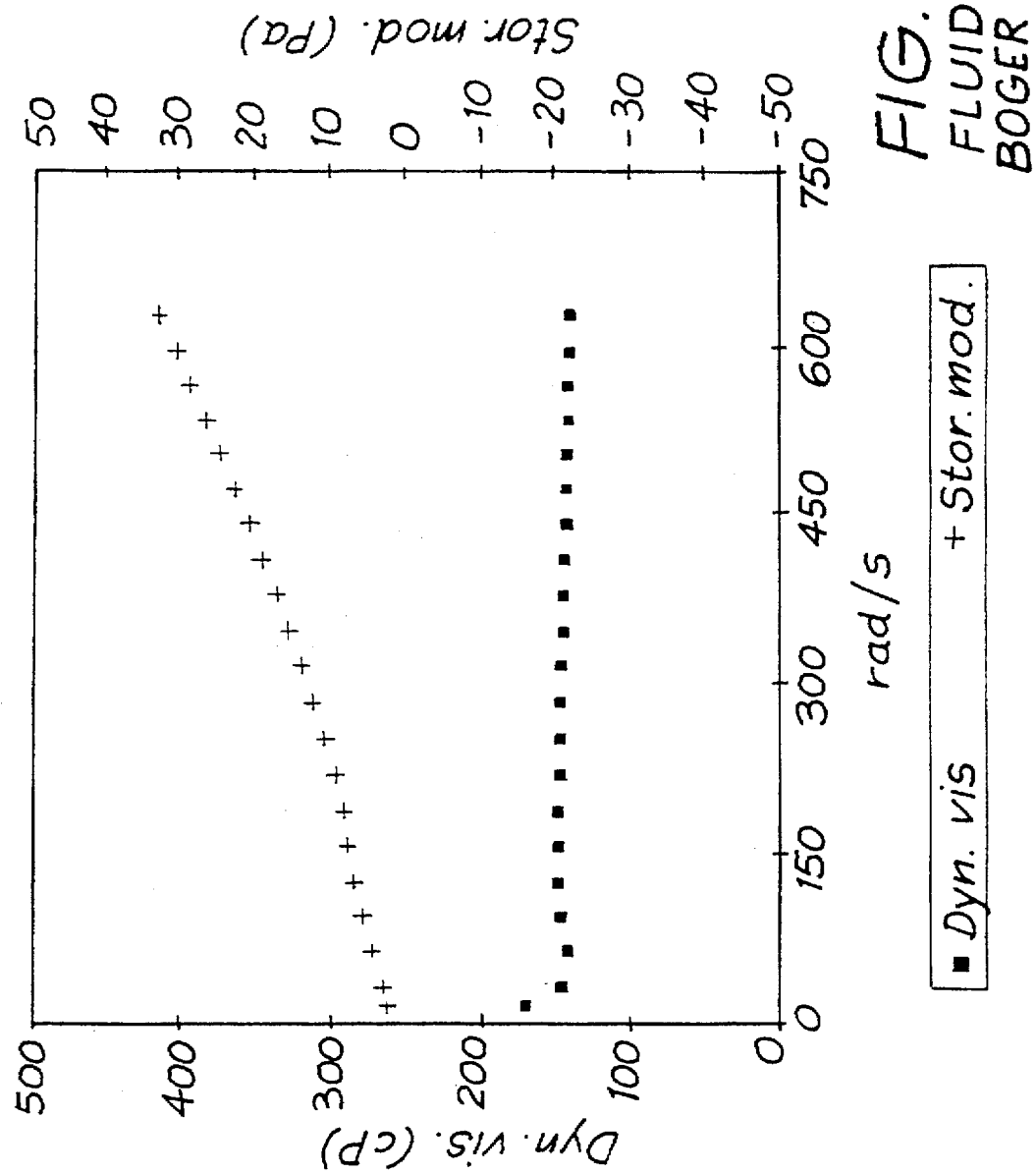

Fluid 2: A light Boger fluid consisting of a high molecular weight (MW of 4 to 6 million) polyisobutylene (0.244%) dissolved in kerosene (6.98%) and diluted with low molecular weight polybutene (marked as Hyvis 3) (93%). Boger fluids were developed to demonstrate non Newtonian behaviour and have been described in detail in a paper by D. B. Boger and M. E. MacKay, "Continuum and molecular interpretation of ideal elastic fluids", J. Non Newtonian Fluid Mechanics 41 (1991) 136–150. The instrument settings were 10 mm upper platen diameter and 1 mm gap. The behaviour measured by the Fourier Micro-rheometer upon interpretation is shown graphically in FIG. 7 and indicates that the fluid has nearly constant dynamic viscosity but increasing stiffness or storage modulus with increasing frequency.

Fluid 3: A dilute solution (10%) of a high molecular weight hyaluronic acid (MW 2.5 million) in distilled water. Hyaluronic acid is a mucopolysaccharide dialysate and an essential component of synovial fluid. Its rheological and chemical structure are discussed in the following paper, P. C. Seller, D. Dowson an V. Wright. "The rheology of synovial fluids", Rheological Acta 10 (1977) 1–7. The instrument settings for the measurement of the rheological properties with the Fourier Micro-rheometer were, upper platen 15 mm diameter and gap setting 0.5 mm. The determined dynamic viscosity and storage modulus with frequency are shown graphically in FIG. 8. The results show that the dynamic viscosity decreases with frequency (commonly called shear thinning) whereas the storage modulus or stiffness increases with frequency.

Thus, there has been described a viscometer for measuring the complex viscosity of small amounts of fluid. Those skilled in the art will appreciate that various modifications can be made to the invention as broadly described without departing from the scope of the invention as claimed. The description should therefore be taken to be illustrative and not restrictive.

What is claimed:

1. A viscometer for determining a complex viscosity of a fluid, the viscometer comprising: vibrating means for imparting an alternating movement to a surface of the fluid without generating a magnetic field to cause a corresponding alternating flow of the fluid, the flow leading the fluid to exert on the vibrating means an alternating reaction force related to the viscosity of the fluid; force measuring means for providing a force signal related to the alternating reaction force; displacement measuring means for providing a movement signal related to the alternating movement of the surface; and processing means for using the force signal and the movement signal to compute the complex viscosity of the fluid, wherein the processor is configured to compute the Fourier transform $F(\omega)$ of the force signal, the Fourier transform $H(\omega)$ of the movement signal, and the ratio $F(\omega)/H(\omega)$ of the Fourier transform of the force signal to the Fourier transform of the movement signal.

2. The viscometer of claim 1 wherein the vibrating means includes two substantially parallel plates one of which is circular and has a radius $\alpha$, the plates being separated by a mean distance h, the fluid being maintained between the two plates, and whenever the processor computes a complex modulus $G^*(\omega)$ of the fluid according to the formula $$G^*(\omega) = \frac{h^3}{3\pi a^4} \frac{F(\omega)}{H(\omega)}.$$

3. A viscometer for determining a complex viscosity of a fluid, the viscometer comprising:

vibrating means for imparting one of a random and a pseudo random alternating movement to a surface of the fluid in a direction substantially perpendicular to the surface to cause a corresponding alternating flow of the fluid, the flow leading the fluid to exert on the vibrating means an alternating reaction force related to the viscosity of the fluid;

force measuring means for providing a force signal related to the alternating reaction force;

displacement measuring means for providing a movement signal related to the alternating movement of the surface; and processing means for using the force signal and the movement signal to compute the complex viscosity of the fluid.

4. The viscometer of claim 3 wherein the vibrating means is an electromechanical shaker.

5. The viscometer of claim 4 wherein the shaker is responsive to a generated control signal.

6. The viscometer of claim 3 wherein the displacement measuring means includes an arrangement that exhibits an electrical capacitance that varies in response to the movement of the surface fluid.

7. The viscometer of claim 3 wherein the force measuring means is a load cell.

8. The viscometer of claim 3 wherein the vibrating means includes a set of coaxial cylinders.

9. The viscometer of claim 3 wherein the movement of the surface is substantially between 0.1 to 1000 Hz.

10. The viscometer of claim 3 wherein the fluid is a non-Newtonian fluid.

11. A method for measuring a viscosity of a fluid, the method comprising the steps of:

imparting an alternating movement to a surface of the fluid to cause a corresponding alternating flow of the fluid, the flow leading the fluid to produce an alternating reaction force related to the viscosity of the fluid;

providing a force signal related to the alternating reaction force;

providing a movement signal related to the alternating movement of the surface; and processing the force signal and the movement signal to compute the viscosity of the fluid by obtaining a Fourier Transform $F(\omega)$ of the force signal, a Fourier transform $H(\omega)$ of the movement signal and a ratio $F(\omega)/H(\omega)$ of the Fourier transform of the force signal to the Fourier transform of the movement signal.

12. A method for measuring a viscosity of a fluid, the method comprising the steps of:

imparting one of a random and a pseudo random alternating movement to a surface of the fluid in a direction substantially perpendicular to the surface to cause a corresponding alternating flow of the fluid, the flow leading the fluid to produce an alternating reaction force related to the viscosity of the fluid;

providing a force related to the alternating reaction force;

providing a movement signal related to the alternating movement of the surface; and processing the force signal and the movement signal to compute the viscosity of the fluid.

13. The method of claim 12 wherein the alternating movement is imparted with an electromechanical shaker.

14. The method of claim 12 wherein displacement is measured by an arrangement that exhibits an electrical capacitance that varies in response to the movement of the surface of the fluid.

15. The method of claim 11 wherein the force is measured by a load cell.

16. The method of claim 11 wherein the alternating movement is imparted by two substantially parallel plates one of which has a radius $\alpha$, the plates being separated by a mean distance h, the fluid being maintained between the two plates, and wherein a complex modulus $G^*(\omega)$ of the fluid is calculated according to the formula $$G^*(\omega) = \frac{h^3}{3\pi\alpha^4} \frac{F(\omega)}{H(\omega)}.$$

17. The method of claim 12 wherein the alternating movement is imparted by placing the fluid between a set of coaxial cylinders.

18. A viscometer comprising:

a fluid sample holder carrying a predetermined amount of fluid, the fluid sample holder having an upper plate spaced from and substantially parallel to a lower plate, the upper plate vibrated at a plurality of frequencies in a direction normal to the plane of the upper plate to produce a reaction force without applying an external magnetic force to the fluid while the lower plate remains substantially motionless;

a force measuring device responsive to the reaction force to produce a force signal;

a displacement device to produce a movement signal indicative of the displacement of the fluid sample holder; and a processing device responsive to the force signal and movement signal to produce the complex viscosity of the fluid.

19. The viscometer of claim 18 wherein the plurality of frequencies are random, pseudo random, or periodic.

20. The viscometer of claim 18 wherein the lower plate has a larger diameter than the upper plate.

21. The viscometer of claim 18 wherein the upper plate and lower plate comprises a pair of coaxial cylinders.

22. The viscometer of claim 18 wherein the displacement device is a non-optical displacement device.

23. The viscometer of claim 18 wherein the complex viscosity is calculated by a Fourier transformation.

* * * * *

UNITED STATES PATENT AND TRADEMARK OFFICE
CERTIFICATE OF CORRECTION

PATENT NO. : 5,750,884
DATED : May 12, 1998
INVENTOR(S) : John S. Field

It is certified that error appears in the above-indentified patent and that said Letters Patent is hereby corrected as shown below:

On the title page item [56], insert --

OTHER DOCUMENTS (Including Author, Title, Date, Pertinent Pages, etc.)
Holly, et al., "Fourier Transform Mechanical Spectroscopy of Viscoelastic Materials With Transient Structure," Journal of Non-Newtonian Fluid Mechanics, 27(1988) 17-26

--.

Signed and Sealed this

Ninth Day of November, 1999

Attest:

Q. TODD DICKINSON

*Attesting Officer*  *Acting Commissioner of Patents and Trademarks*